United States Patent [19]

Karrer

[11] 3,998,855
[45] Dec. 21, 1976

[54] EPOXYALKOXY SUBSTITUTED BENZOPHENONES

[75] Inventor: Friedrich Karrer, Basel, Switzerland

[73] Assignee: CIBA-GEIGY Corporation, Ardsley, N.Y.

[22] Filed: July 1, 1974

[21] Appl. No.: 484,724

Related U.S. Application Data

[63] Continuation of Ser. No. 321,625, Jan. 8, 1973, abandoned.

[30] Foreign Application Priority Data

Jan. 14, 1972 Switzerland .......................... 523/72
Dec. 13, 1972 Switzerland ..................... 18174/72

[52] U.S. Cl. ........................... 260/348 R; 260/591; 424/278; 424/DIG. 8
[51] Int. Cl.² ....................................... C07D 303/32
[58] Field of Search ............................... 260/348 R

[56] References Cited

UNITED STATES PATENTS

| | | | |
|---|---|---|---|
| 3,697,543 | 10/1972 | Pfiffner et al. .................. | 260/327 E |
| 3,711,519 | 1/1973 | Dolejs et al. ................... | 260/348 R |
| 3,873,620 | 3/1975 | Pinhas ........................... | 260/348 R |
| 3,892,799 | 7/1975 | Pinhas ........................... | 260/348 R |
| 3,944,531 | 3/1976 | Chodnekar et al. ............ | 260/348 R |

FOREIGN PATENTS OR APPLICATIONS 475,242    8/1969    United Kingdom

OTHER PUBLICATIONS

Chemical Abstracts, vol. 72 (1970) 111512z.

*Primary Examiner*—Norma S. Milestone
*Attorney, Agent, or Firm*—Harry Falber

[57] ABSTRACT

4-Alkoxy-benzophenone derivatives of the formula

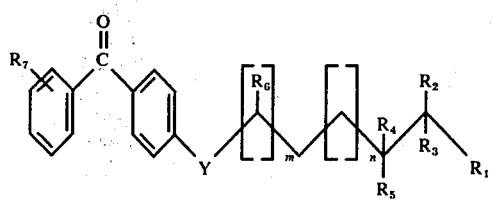

wherein $R_1$ represents hydrogen, halogen, alkyl with 1 to 4 carbon atoms, vinyl or ethinyl, $R_2$ represents hydrogen, halogen, halogen methyl or ethyl, or $R_1$ and $R_2$ together represent the cyclopentyl or cyclohexyl ring, $R_3$ represents hydrogen, halogen, methyl, ethyl or alkoxy with 1 to 4 carbon atoms, $R_4$ represents hydrogen, halogen or methyl, $R_5$ represents hydrogen or halogen or $R_3$ and $R_5$ together represent a carbon to carbon bond or an oxygen bridge, $R_6$ represents hydrogen, methyl or ethyl, $R_7$ represents hydrogen, halogen, alkyl or alkoxy, each with 1 to 4 carbon atoms, Y represents oxygen or the group —CH₂O—, wherein the CH₂ group is bonded to the phenyl nucleus, and n and m is each 0 or 1, their manufacture and their use in combating insects and representatives of the order Acarina.

4 Claims, No Drawings

EPOXYALKOXY SUBSTITUTED BENZOPHENONES

This is a continuation of application Ser. No. 321,625, filed on Jan. 8, 1973, now abandoned.

The invention relates to 4-alkoxy-benzophenone derivatives which are unsubstituted or substituted in the phenyl nuclei, and to their manufacture and use in combating insects and representatives of the order Acarina.

The compounds correspond to the formula

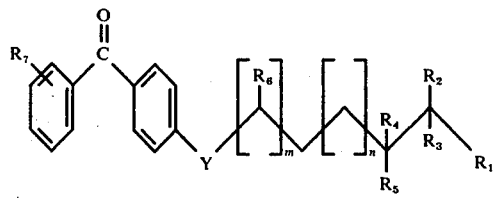

wherein $R_1$ represents hydrogen, halogen, alkyl with 1 to 4 carbon atoms, vinyl or ethinyl, $R_2$ represents hydrogen, halogen, halogen methyl or ethyl, or $R_1$ and $R_2$ together represent the cyclopentyl or cyclohexyl ring, $R_3$ represents hydrogen, halogen, methyl, ethyl or alkoxy with 1 to 4 carbon atoms, $R_4$ represents hydrogen, halogen or methyl, $R_5$ represents hydrogen or halogen or $R_3$ and $R_5$ together represent a carbon to carbon bond or an oxygen bridge, $R_6$ represents hydrogen, methyl or ethyl, $R_7$ represents hydrogen, halogen, alkyl or alkoxy, each with 1 to 4 carbon atoms, Y represents oxygen or the group —$CH_2O$—, wherein the $CH_2$ group is bonded to the phenyl nucleus, and n and m is each 0 or 1.

By halogen is meant fluorine, chlorine, bromine or iodine, but in particular chlorine.

The alkyl and alkoxy groups which are possible for $R_1$, $R_3$ and $R_7$ can be straight-chain or branched. Examples of such groups include: methyl, ethyl, propyl, isopropyl, i—, n—, sec. and tert.butyl, methoxy, ethoxy.

A preferred group of compounds is that of the formula I, wherein $R_1$ represents hydrogen, chlorine, methyl, ethyl, n-propyl, isopropyl, n—, i—, sec. and tert.butyl, vinyl or ethinyl, $R_2$ represents hydrogen, chlorine, methyl or ethyl, or $R_1$ and $R_2$ together represent the cyclopentyl or cyclohexyl ring, $R_3$ represents hydrogen, methyl, ethyl, methoxy or alkoxy, $R_4$ represents hydrogen, chlorine or methyl, $R_5$ represents hydrogen or $R_3$ and $R_5$ together represent a carbon to carbon bridge, $R_6$ represents hydrogen or methyl, $R_7$ represents hydrogen, chlorine, methyl or methoxy, Y represents oxygen or the group —$CH_2O$-, wherein the $CH_2$ group is bonded to the phenyl nucleus, and n and m is each 0 or 1.

To be particularly highlighted on account of their action are the compounds of the formula I wherein $R_1$ represents hydrogen, chlorine, methyl, ethyl, n-propyl, isopropyl, n-, i- and sec. butyl or ethinyl, $R_2$ represents hydrogen, chlorine, methyl or ethyl, $R_3$ represents hydrogen, methyl, methoxy or ethoxy, $R_4$ represents hydrogen or chlorine, $R_5$ represents hydrogen, or $R_3$ and $R_5$ together represent a carbon to carbon bond or an oxygen bridge, $R_6$ represents hydrogen or methyl, $R_7$ represents hydrogen, Y represents oxygen and n and m is each 0 or 1.

The compounds of the formula I are manufactured in a manner known per se by the following methods:

1. formation of the ether (O-alkylation) by condensing a halide with a 4-hydroxybenzophenone derivative:

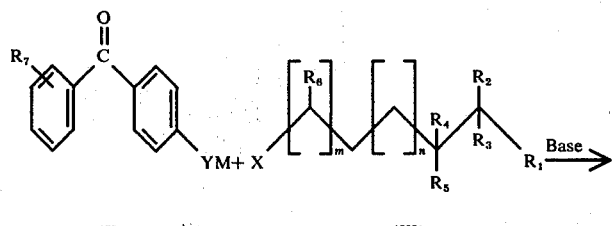

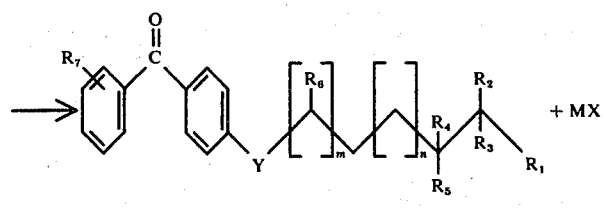

wherein in the formulae II and III $R_1$ to $R_7$, Y, m and n also have the meanings given for the formula I; X represents chlorine, bromine or iodine, preferably chlorine or bromine; M is a metal, in particular one of the main group I or II of the Periodic System, or is hydrogen;

2. epoxidation of a 4-alkenyloxy-benzophenone derivative:

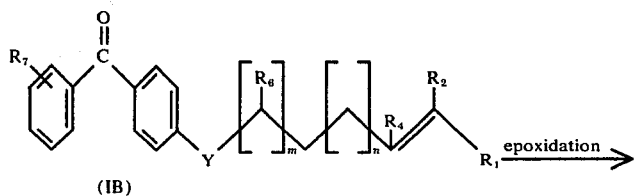

(IB)

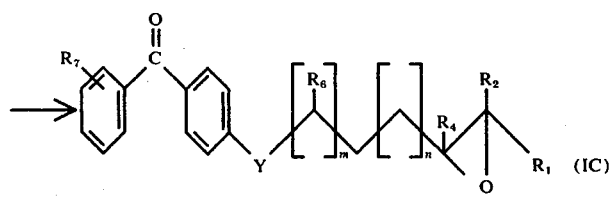

(IC)

3. addition of hydrogen halide to the olefinic double bond of a 4-alkenyloxy derivative:

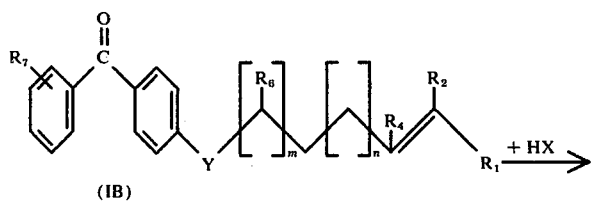

(IB)

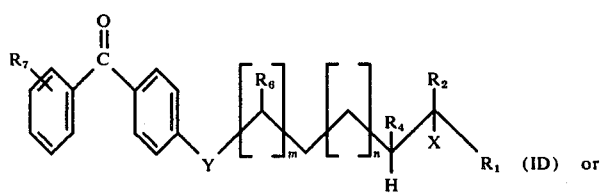

(ID) or

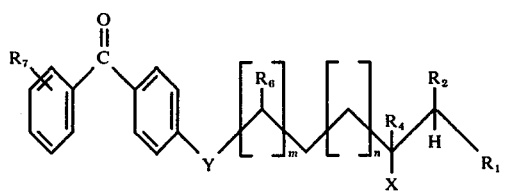

wherein in the formulae (IB) and (ID) $R_1$, $R_2$, $R_4$, $R_6$, $R_7$, Y, m and n have the meanings given for the formula I, and X represents halogen, but preferably chlorine;

4. epoxidation of an unsaturated halide to an epoxy halide and condensation thereof with a 4-hydroxybenzophenone derivative:

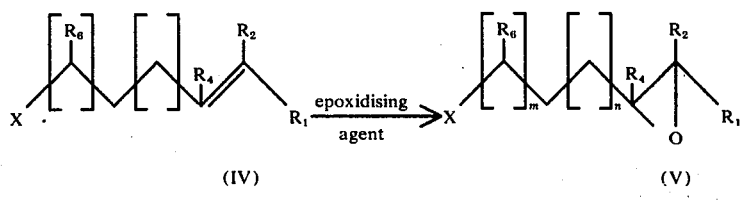

(IV)      (V)

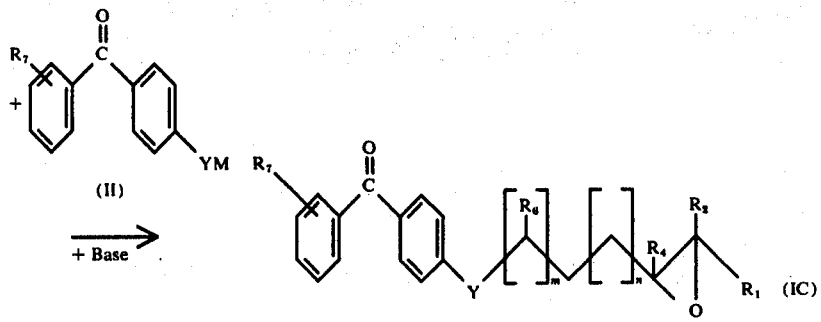

wherein in the formulae IC, II, IV and V $R_1$, $R_2$, $R_4$, $R_6$, $R_7$, Y and n and m have the meanings given hereinbefore, and X represents halogen, in particular bromine or chlorine;

wherein $R_1$, $R_2$, $R_4$, $R_6$, $R_7$, Y, m and n have the meanings given for the formula I;

6. addition of an alcohol or water to a double bond:

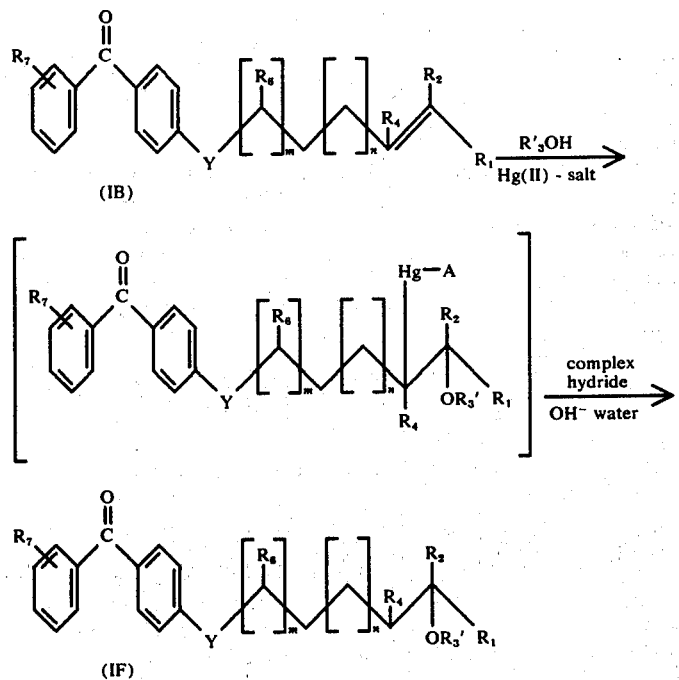

wherein $R_1$, $R_2$, $R_4$, $R_6$, $R_7$, Y, m and n have the meanings given for the formula I, A represents the anion of 5. hydrogenation of a 4-alkenyloxy-benzophenone derivative:

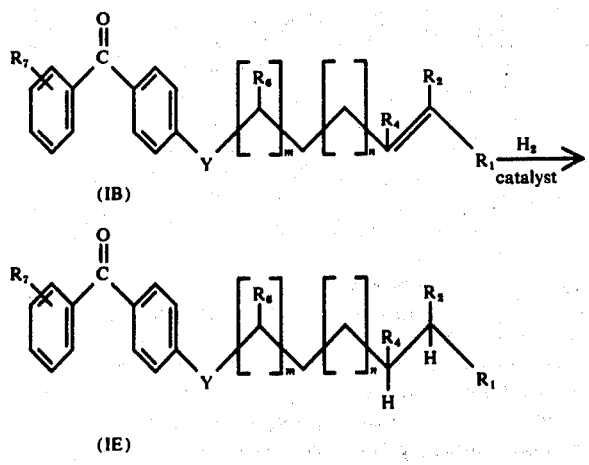

a Hg(II) salt and $R_3'$ represents an alkyl radical with 1 to 4 carbon atoms or hydrogen;

7. manufacture of the alcohol and etherification of the OH group:

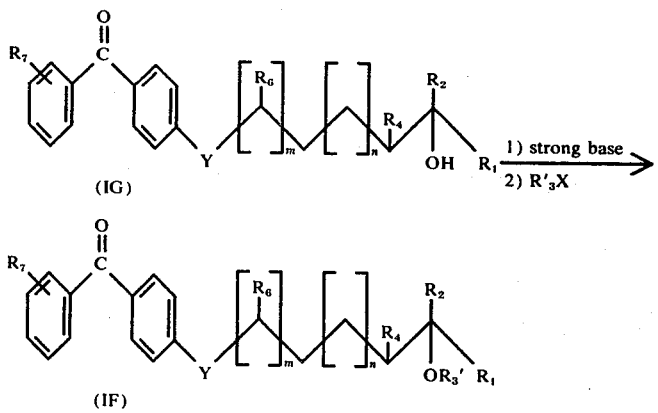

wherein $R_1$, $R_2$, $R_4$, $R_6$, $R_7$, Y, m and n have the meanings given for the formula I, X represents a halogen atom and $R_3'$ represents an alkyl radical with 1 to 4 carbon atoms.

The O-alkylations of the 4-hydroxy- or 4-hydroxymethyl-benzophenone, or their derivatives which are substituted in the nucleus, can be carried out with the various saturated or unsaturated halides, depending upon the reactivity of the halide employed, in various solvents and at varying reaction temperatures, but always in the presence of at least 1 mole of one of the bases cited hereinbelow.

Suitable solvents are chiefly: acetone, methyl ethyl ketone, cyclohexanone, 1,2-dimethoxyethane, tetrahydrofuran, dioxan, dialkyl ether, dimethyl formamide, dimethyl sulphoxide, hexamethylphosphoric triamide, sulpholane, inert hydrocarbons, such as toluene, benzene, xylene and the like. But it is also possible to use further solvents.

As necessary bases or acid acceptors in the ether formation from the 4-hydroxybenzophenone derivative and a halide there are used primarily alkali or alkaline earth hydroxides, alkali or alkaline earth carbonates, alkali or alkaline earth hydrides and alkali alkoxides. But organic bases, for example triethylamine, pyridine etc., can also be used as acid acceptors.

The reaction temperatures of the arylether formation are between −10° and 140° C, mostly between 5° and 70° C (e.g. when using solvents such as dimethyl sulphoxide, dimethyl formamide, sulpholane, hexamethylphosphoric triamide, 1,2-dimethylethane etc.), or at the boiling temperature of the solvent employed (e.g. in the case of ketones).

The conversion of the benzophenone alkenyl ether to the corresponding epoxy derivatives is carried out preferably in an inert solvent, advantageously a chlorinated hydrocarbon, between −25° C and room temperature, mostly between −5° and +5° C, with the aid of an epoxidising agent, for example a paracid. The epoxy derivatives of the formula IB can also be obtained via the corresponding halohydrines by dehydrohalogenation, wherein a benzophenone alkenyl ether is converted into the bromohydrine with a N-halosuccinamide, e.g. with N-bromosuccinamide, in a mixture of water and a solvent such as tetrahydrofuran, 1,2-dimethoxyethane, dioxan or tert. butanol, in homogeneous or heterogeneous phase between −5° C and room temperature, and the desired epoxy derivative is obtained by subsequently treating the bromohydrine with an alkaline agent, for example alkali carbonate, alkali alkoxide or an alkali hydroxide. Alkali is to be understood as meaning in particular sodium and potassium.

The term "peracid" is to be understood as comprising chiefly peralkane acids with 1 to 6 carbon atoms, e.g. peracetic acid, also aromatic peracids such as perbenzoic acid, monoperphthalic acid, but in particular 3-chloroperbenzoic acid.

The working up and isolation of compounds of the formula I are carried cut by known methods, e.g. treating the reaction mixture with water or ice, subsequent extraction with a suitable solvent, e.g. ether, washing the organic phase, e.g. with dilute alkali lye, and drying the solution over sodium sulphate. After the solvent has been removed it is possible to purify the residual compound of the formula I - if necessary - by crystallisation, vacuum distillation, or chromatography on silica gel or aluminum oxide.

Various reaction sequences are possible in order to obtain benzophenone alkyl ethers of the formula IC: either firstly the 4-hydroxy- or 4-hydroxymethyl-benzophenone compound is etherified in the presence of a base with an alkenyl halide according to the manufacturing process cited hereinbefore, and subsequently the olefinic double bond in this aryl-alkenyl ether is converted into an epoxide as described above, or firstly the alkenyl halide is epoxidised under anhydrous conditions in an inert solvent, advantageously in a chlorinated hydrocarbon, between −25° C and room temperature, with the aid of an epoxidising agent, for example a paracid, and this epoxy halide is reacted in the secondary reaction with the 4-hydroxy- or 4-hydroxymethyl-benzophenone, in the presence of an acid acceptor, to give the end product.

The addition of hydrogen halide, in particular of hydrogen chloride or bromide, to the aliphatic double bond is preferably effected by treating a benzophenone alkenyl ether with anhydrous hydrogen halide in a suitable solvent, e.g. methanol, ethanol, some other alcohol, a dialkyl ether, 1,2-dimethoxyethane, glacial acetic acid etc. The addition of the hydrogen halide is carried out at a temperature between −30° and +25° C.

The halide formed is isolated, as mentioned hereinbefore, by methods which are known in the art, such as treatment of the reaction mixture with water, extraction with an organic solvent and removal of the excess hydrogen halide by neutralisation with a weak base or by washing with water, and, upon removal of the solvent, the residual halide can be further purified by crystallisation, distillation in a high vacuum, or by chromatography.

Unsaturated araliphatic ethers of the formula IB can be hydrogenated in known manner to give the saturated araliphatic ethers of the formula IE with catalytically activated hydrogen, expediently between room temperature and the boiling temperature of the reaction mixture at normal or elevated pressure. Suitable catalysts are preferably Raney nickel or noble metals such as platinum or palladium. Suitable solvents are chiefly methyl and ethyl acetate, dioxan or alcohols, such as methanol or ethanol.

The reactions to give the active substance of the formula I, wherein $R_3$ represents an alkoxy group with 1 to 4 carbon atoms, are carried out at normal pressure and in an anhydrous alcohol $R_3'OH$ and, optionally, in solvents and diluents which are inert otwards the reactants, for example in ethers such as tetrahydrofuran, dioxan, diethyl ether, 1,2-dimethoxyethane etc. In the first step - if $R_3' = H$ - and in the second step, it is also possible to use water as solvent.

As mercury (II) salts there are preferably used mercury-(II)-acetate and mercury-(II)-trifluoroacetate. MeBH$_4$ is used as complex hydride, wherein Me represents an alkali or alkaline earth metal atom. The reaction with complex boron hydride takes place in the presence of alkali hydroxide and water. The reaction temperatures are in the range from $-10°$ to $+40°$ C. and are preferably between $0°$ and $+25°$ C.

As a further method of obtaining compounds of the formula I, wherein $R_3$ represents an alkoxy group with 1 to 4 carbon atoms, it is also possible to carry out the etherification of an alcohol of the formula IG by reaction with a halide, depending upon the reactivity of the halide employed, in various solvents and at varying reaction temperatured, but always in the presence of at least one mole of one of the above cited bases.

Where this is possible in principle, the resulting compounds occur as cis/trans isomer mixtures. An isomer mixture can be resolved into the isomeric forms e.g. with the aid of chromatographic separating methods, for example by adsorption to a separating material with selective adsorption activity, e.g. silica gel, aluminium oxide, and subsequent elution of the separated isomers with a suitable solvent, e.g. diethyl ether, hexane, methyl or ethyl acetate. A further chromatographic separating method is gras chromatography. In certain cases it is also possible to resolve an isomer mixture by means of fractional distillation or fractional crystallisation.

The starting materials of the formulae II to IV are known compounds which can be manufactured analogous to known methods described in the literature.

The compounds of formula I are suitable for combating various animal and plant pests. They are suitable for combating insects and representatives of the order Acarina, but above all for combating insects.

The compounds of the formula I can therefore be used for example against the following orders and families:

| | |
|---|---|
| Orthoptera | Acrididae |
| | Gryllidae |
| | Blattidae |
| Isoptera | Kalotermitidae |
| Hemiptera | Miridae |
| | Piesmidae |
| | Lygaeidae |
| | Pyrrhocoridae |
| | Pentatomidae |
| | Cimicidae |
| | Reduviidae |
| | Jassidae |
| | Eriosomatidae |
| | Lecaniidae |
| Coleoptera | Carabidae |
| | Elateridae |
| | Coccinellidae |
| | Tenebrionidae |
| | Dermestidae |
| | Cucujidae |
| | Chrysomelidae |
| | Curculionidae |
| | Scolytidae |
| | Scarabacidae |
| Lepidoptera | Pyralidae |
| | Phyticidae |
| | Pyraustidae |
| | Crambidae |
| | Tortricidae |
| | Galleriidae |
| | Lyonetiidae |
| | Yponomeutidae |
| | Pieridae |
| | Plutellidae |
| | Lymantriidae |
| | Noctuidae |
| Diptera | Culicidae |
| | Simuliidae |
| | Tipulidae |

The insecticidal and/or acaricidal action can be substantially broadened and adapted to suit the particular circumstances by the addition of other insecticides and/or acaricides.

Organic Phosphorus Compounds

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION) O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)

O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4,5-trichlorophenylthiophosphate (RONNEL)
O-ethyl-O,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-iodophenyl)-thiophosphate (JODOFENPHOS)
4-tert.butyl-2-chlorophenyl-N-methyl-O-methylamidophosphate (CRUFOMATE)
O,O-dimethyl-O-(3-methyl-4-methylmercaptophenyl)thiophosphate (FENTHION)
Isopropylamino-O-ethyl-O-(4-methylmercapto-3-methylphenyl)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxime-O,O-diethylthiophosphate (PHOXIM)
O,O-diethyl-O-(3-chloro-4-methyl-2-oxo-2-H-1-benzopyran-7yl)-thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)-thiophosphate (DIAZINON)
O,O-diethyl-O-(2-quinoxalyl)thiophosphate
O,O-dimethyl-S-(4-oxo-1,2,3-benzotriazin-3(4H)-ylmethyl)-dithiophosphate (AZINPHOS-METHYL)
O,O-diethyl-S-(4-oxo-1,2,3-benzotriazin-3(4H)-ylmethyl)-dithiophosphate (AZINPHOSETHYL)
S-[(4,6-diamino-s-triazin-2-yl)methyl]O,O-dimethyl-dithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2(O,O-dimethyl-phosphoryl-thiomethyl)-5-methoxypyrone-4-3,4-dichlorobenzyl-triphenylphosphoniumchloride
O,O-diethyl-S-(2,5-dichlorophenylthiomethyl)dithiophosphate (PHENKAPTON)
O,O-diethyl-O-(4-methyl-cumarinyl-7)-thiophosphate (POTASAN)
5-amino-bis(dimethylamido)phosphinyl-3-phenyl-1,2,4-triazole (TRIAMIPHOS)
N-methyl-5-(O,O-dimethylthiophosphoryl)-3-thiavaleramide (VAMIDOTHION)
O,O-diethyl-O-[2-dimethylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
dimethyl-p-(methylthio)phenylphosphate
O,O-dimethyl-O-p-sulphamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-siobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O(5-phenyl-3-isooxazolyl)thiophosphate 2-(diethoxyphosphinylimino)-4-methyl-1,3-dithiolane
tris-(2-methyl-1-aziridinyl)-phosphine oxide (METEPA) S-(2-chloro-1-phthalimidoethyl)-O,O-diethyldithiophosphate
N-hydroxynaphthalimido-diethylphosphate
dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
diethyl-S-2-(ethylsulphinyl)ethyl dithiophosphate (OXIDISULFOTON)
bis-O,O-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
O,O-dimethyl-O-(2,2-dichloro-1-methoxy-vinyl)-phosphate
bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)phosphate O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
diisopropylaminofluorophosphate (MIPAFOX)
O,O-dimethyl-S-(morpholinylcarbamoylmethyl)dithiophosphate (MORPHOTHION)
bismethylamido-phenylphosphate
O,O-dimethyl-S-(benzenesulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
O-phenyl-O-p-nitrophenyl-metharethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide O,O-di-($\beta$-chloroethyl)-O-(3-choro-4-methyl-coumarinyl-7)-phosphate
S-(1-phthalimidoethyl)-O,O-diethyldithiophosphate
O,O-dimethyl-O-(3-chloro-4-diethylsulphamyl-phenyl)-thiophosphate
O-methyl-O-(2-carbisopropoxyphenyl)-amidothiophosphate
5-(O,O-dimethylphosphoryl)-6-chloro-bicyclo(3.2.0)-heptadiene(1,5)
O-methyl-O-(2-i-propoxycarbonyl-1-methylvinyl)-ethylamidothiophosphate.

NITROPHENOLS AND DERIVATIVES 4,6-dinitro-6-methylphenol,sodium salt [Dinitrocresol]
dinitrobutylphenol-(2,2',2")-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6dinitrophenyl-cyclopropionate
2sec.-butyl-4,6-dinitrophenylisopropylcarbonate [Dinobuton]

MISCELLANEOUS pyrethin I
pyrethin II
3-allyl-2-methyl-4-oxo-2-cyclopentan-1-yl-crysanthemumate (Allethrin)
6-chloroproperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-4-oxocyclopent-2-enyl-(I)-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-phenoxycarbamyl-2-trifluoromethylbenzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

FORMAMIDINES 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine 1-n-butyl-1-methyl-2-(2-methyl-4-chlorophenyl)-formamidine
1-methyl-1-(2-methyl-4-chloroaniline-methylene)-formamidine
2-(2-methyl-4-chlorophenyl-formamidine
1-n-butyl-1-(2-methyl-4-chlorophenyl-imino)-pyrolidine.

UREA

N-2-methyl-4-chlorophenyl-N',N'-dimethyl-thiourea.

CARBAMATES 1-naphthyl-N-methylcabamate (CARBARYL)
2-butinyl-4-chlorophenylcarbamate
4-dimethylamino-3,5-xylyl-N-methylcabamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-melthyl-2-methylthio-propionaldehyde-O-(methylcarbamoyl)-oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)-phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithiolane-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethyl-carbamate
O-(2,2-dimethyl-4-chloro-2,3-dihydro-7benzofuranyl)-N-methylcarbamate
O-(2,2,4-trimethyl-2,3-dihydro-7-benzofuranyl)-N-methylcarbamate
O-naphthyl-N-methyl-N-acetal-carbamate
O-5,6,7,8-tetrahydronphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3(α-methoxymethyl-2-propenyl)-phenyl-N-methyl-carbamate
2-chloro-5-tert.butyl-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate 1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylmino]-3-tolyl-N-methylcarbamate
4-[dipropargylaminol]-3,5-xylyl-N-methylcarbamate
2-[allyl-isopropylamino]-phenyl-N-methylcarbamate
3-[allyl-isopropylamino]-phenyl-N-methylcarbamate

CHLORINATED HYDROCARBONS

γ-hexachlorocyclohexane [GAMMEXANE; LINDAN; γ HCH]
1,2,4,5,6,7,8,8-octachloro-3α,4,7,7α'tetrahydro-4,7-methylene indane [CHLORDAN]
1,4,5,6,7,8,8-heptachloro,3α,4,7,7α-tetrahydro-4,7-methylene indane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-octahydro-exo-1,4,endo-5,8-dimethanonaphthalene [DIFLORIN]
1,2,3,4,10,10-hexachloro-5,7-epoxy-1,4,4α,5,6,7,8,8α-octyhydro-endo-endo-5,8-dimethanonaphthalene [ENDRIN]

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

SOLID FORMS:

Dusts, tracking agents, granules, coated granules, impregnated granules and homogeneous granules.

LIQUID FORMS:

a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminum silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active subsances of the formula I with polymersible compounds (urea/formaldehyde; dicyandiamide/formaldehyde; malamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkanline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agent which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldhyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, the size of the solid particles does not exceed 0.02 to 0.04 $\mu$ in wettable powders, and 0.03 $\mu$ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions in which boil between 120° and 350° C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic or aromatic hydrocarbons, chlorinated derivatives thereof, alkyl naphthalenes, and mineral oils, singly or in admixture with each other, can be used as organic solvents.

The content of active substance in the above described agents is between 0.1 to 95 percent, in which connection it should be mentioned that, in the case of application from aircraft or some other suitable means of application, it is possible to use concentrations of up to 99.5 percent or even pure active substance.

The active substances of the formula I can, for example, be formulated as follows:

DUSTS

The following substances are used to manufacture a) a 5% and b) a 2% dust:
  a. 5 parts of active substance 95 parts of talcum
  b. 2 parts of active substance 1 part of highly disperse silicic acid 97 parts of talcum.

The active substances are mixed with the carriers and ground.

GRANULES

The following substances are used to produce 5% granules:
  5 parts of active substance,
  0.25 parts of epichlorhydrin,
  0.25 parts of cetyl polyglycol ether,
  3.50 parts of polyethylene glycol,
  91 parts of kaolin (particle size 0.3 – 0.8 mm).

The active substance is mixed with epichlorohydrin and dissolved with 6 parts of acetone; the polyethylene glycol and cetyl polygylcol ether are then added. The thus obtained solution is sprayed on kaolin, and the acetone subsequently evaporated in vacuo.

WETTABLE POWDER:

The following constituents are used for the preparation of a) a 40%, b) and c) a 25%, and d) a 10% wettable powder:
  a. 40 parts of active substance,
    5 parts of sodium lignin sulphonate,
    1 part of sodium dibutyl-naphthalene sulphonate,
    54 parts of silicic acid.
  b. 25 parts of active substance,
    4.5 parts of calcium lignin sulphonate,
    1.9 parts of Champagne chalk/hydroxyethyl cellulose mixture (1:1),
    1.5 parts of sodium dibutyl naphthalene sulphonate,
    19.5 parts of silicic acid,
    19.5 parts of Champagne chalk,
    28.1 parts of kaolin.
  c. 25 parts of active substance,
    2.5 parts of isooctylphenoxy-polyoxyethyleneethanol,
    1.7 parts of Champagne chalk/hydroxyethyl cellulose mixture (1:1),
    8.3 parts of sodium aluminium silicate,
    16.5 parts of kieselguhr,
    46 parts of kaolin.
  d. 10 parts of active substance,
    3 parts of a mixture of the sodium salts of saturated fatty alcohol sulphates,
    5 parts of naphthalenesulphonic acid/formaldehyde condensate,
    82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

EMULSIFIABLE CONCENTRATES:

The following substances are used to produce a) a 10% and b) a 25% emulsifiable concentrate:
  a. 10 parts of active substance,
    3.4 parts of epoxidised vegetable oil,
    13.4 parts of a combination emulsifier consisting of fatty alcohol polyglycol ether and alkylarylsulphonate calcium salt,
    40 parts of dimethylformamide,
    43.2 parts of xylene.
  b. 25 parts of active substance,
    2.5 parts of epoxidised vegetable oil,
    10 parts of an alkylarylsulphonate/fatty alcoholpolyglycol ether mixture
    5 parts of dimethylformamide,
    57.5 parts of xylene.

From these concentrates it is possible to produce, by dilution with water, emulsions of any desired concentration.

SPRAY:

The following constituents are used to prepare a 5% spray:
  5 parts of active substance,
  1 part of epichlorhydrin, 94 parts of benzine (boiling limits 160° – 190° C).

EXAMPLE 1

While stirring vigorously, 6.7 g of 90% pulverised potassium hydroxide were added by small amounts at 10°–15° C within 5 hours to a solution of 19.8 g of 4-hydroxybenzophenone and 20.5 g of 2-bromo-6-methyl-3-octene in 200 ml of dimethyl sulphoxide. After the addition of the potassium hydroxide stirring was continued for 16 hours at room temperature. For the working up, the reaction mixture was stirred in one litre of ice water, the organic isolated and the aqueous layer extracted 4 times with diethyl ether. The combined organic phases were then washed repeatedly with ice cold 10% aqueous potassium hydroxide and finally with water until neutral, dried over sodium sulphate and the solvent and volatile constituents were completely distilled off in vacuo, to leave as residue analytically pure, colourless 4-(1,5-dimethyl-4-heptenyl-1-oxy)-benzophenone. $n_D^{20}$: 1.5680.

EXAMPLE 2

A. While stirring, a solution of 6.5 g of app. 86% potassium hydroxide in 100 ml of absolute ethanol was added dropwise at room temperature to a solution of 19.8 g of 4-hydroxybenzophenone and 16.4 g of 1-bromo-3-methyl-2-pentene in 150 ml of 1,2-dimethoxyethane. After the addition of the base, stirring was continued for 15 hours at room temperature. For the processing, the potassium bromide which had formed was filtered off and the filtrate concentrated in vacuo. The residue was taken up in ether/n-hexane (1:2), and washed with ice cold 10% potassium hydroxide solution and subsequently with water until neutral. The organic phase was dried over sodium sulphate, filtered, and the solvent removed, to leave a residue the colourless, analytically pure 4-(3-methyl-cis/trans-2-pentenyl-1-oxy)-benzophenone, which congealed to a crystalline solid and was recrystallised from n-hexane. Melting point: 32°–34° C.

B. A solution of 10.15 g of 85% 3-chloroperbenzoic acid in 100 ml of methylene chloride/diethyl ether (9:1) was added dropwise at −2° to 0° C within 4 hours of a solution of 14 g of 4-(3-methyl-2-pentenyl-1-oxy)-benzophenone in 150 ml of methylene chloride. The reaction mixture was stirred for 2 hours at 0° C, then treated with n-hexane, and washed 3 times with ice cold 10% potassium hydroxide solution and then with water until neutral. The solution was dried over sodium sulphate, filtered, the solvent completely removed in vacuo, and the residue gradually congealing to a crystalline solid was recrystallised for cyclohexane, to give pure 4-(2,3-epoxy-3-methyl-pent-1-oxy)-benzophenone (m.p. 66°–67° C).

EXAMPLE 3

To a mixture of 19.8 g of 4-hydroxybenzophenone and 20 g of pulverised, anhydrous potassium carbonate in 150 ml of acetone were added dropwise at 55° C within 30 minutes 13.3 g of cis/trans-1,3-dichloropropene and the reaction mixture was kept for 18 hours at reflux temperature. Solids were filtered off from the reaction solution and the bulk of the acetone was removed from the filtrate in vacuo. The residue was taken up in diethyl ester and the ethereal solution was washed 6 times with 10% potassium hydroxide solution and 4 times with water. The organic phase was dried over sodium sulphate, the solvent completely removed and the crystalline congealing residue was recrystallised from methanol to give cis, trans-4-(3-chloro-2-propenyl-1-oxy)-benzophenone (m.p. 56°–59° C).

EXAMPLE 4

While stirring vigorously, a solution of 14.1 g of 4-(3-methyl-2-pentenyl-1-oxy)-benzophenone in 70 ml of absolute methanol was added in 8 minutes to a suspension cooled to −5° C of 19.1 g of pulverised mercury(II)-acetate in 120 ml of absolute methanol. Two hours after the addition of the olefine the reaction mixture was cooled to −18° C and treated with 60 ml of a 3 molar aqueous sodium hydroxide solution, whereby the temperature rose to −5° C (cooling bath −20° C). Fifteen minutes after the addition of the sodium hydroxide the reaction mixture was treated at about −8° C with 60 ml of 0.5 n sodium borohydride solution in 3 n sodium hydroxide solution and the temperature was allowed to rise gradually to 0° C. Two and a half hours after the addition of the borohydride solution the precipitated mercury slurry was decanted from the reaction mixture by pouring the supernatant solution on 600 ml of saturated sodium chloride solution and extracting 4 times in a separating funnel with 200 ml of diethyl ether. The combined ethereal solutions were washed 4 times with sodium chloride solution, dried over sodium sulphate and completely freed from solvent in vacuo. The oily residue was purified by chromatography on silica gel (eluant: diethyl ether/hexane 1:3) to give pure 4-(3-methyl-3-methoxy-pent-1-oxy)-benzophenone. $n_D^{20}$: 1.5678. The following compounds were also manufactured in analogous manner:

| Active Substance | Physical Data |
|---|---|
| 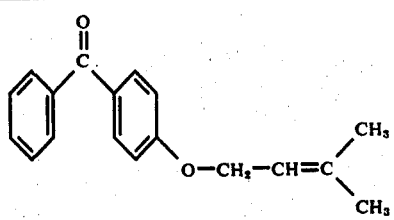 | m.p.: 59–60° C |

-continued
| Active Substance | Physical Data |
|---|---|
| 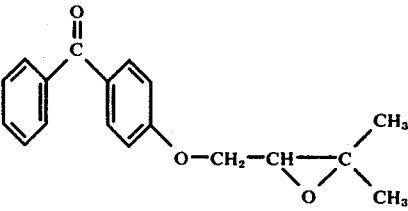 | m.p.: 63–65° C |
| 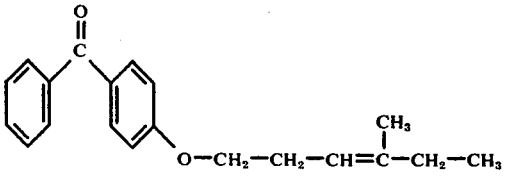 | $n_D^{21}$: 1,5814 |
| 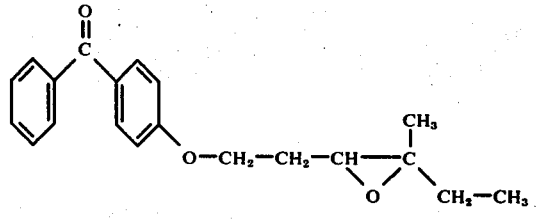 | $n_D^{20}$: 1,5751 |
| 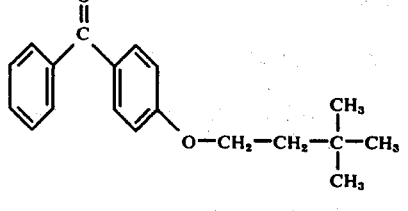 | $n_D^{20}$: 1,5697 |
| 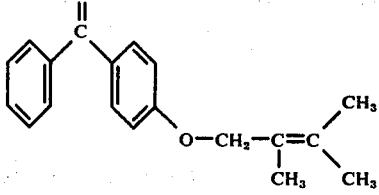 | m.p.: 94–96° C |
| 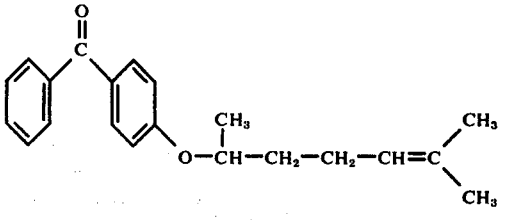 | $n_D^{20}$: 1,5721 |
| 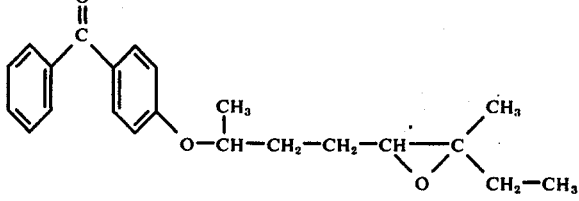 | $n_D^{20}$: 1,5693 |

-continued
| Active Substance | Physical Data |
|---|---|
| 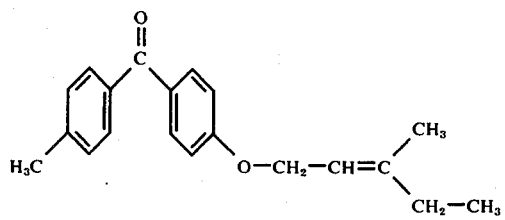 | m.p.: 31–33° C |
| 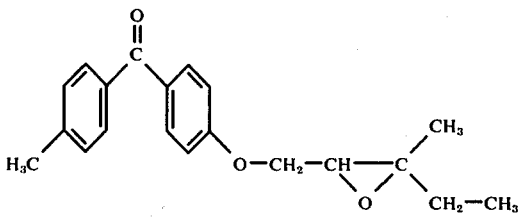 | m.p.: 41–43° C |
| 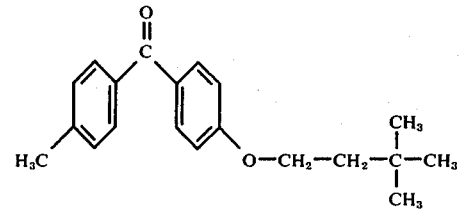 | m.p.: 36–38° C |
| 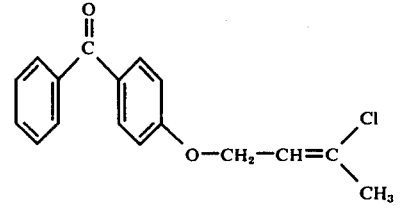 | m.p.: 60–62° C |
| 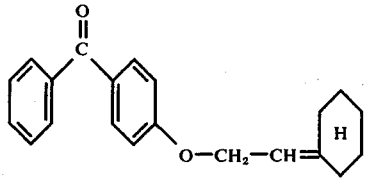 | m.p.: 99–100° C |
| 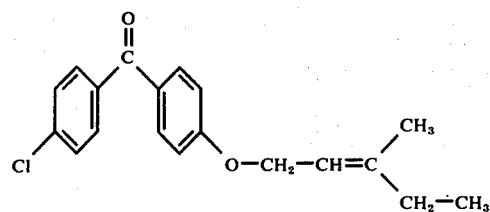 | m.p.: 85–87° C |
| 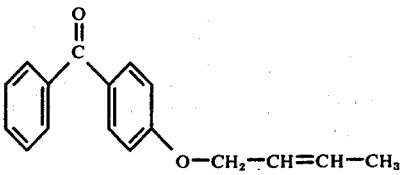 | m.p.: 34–36° C |
| 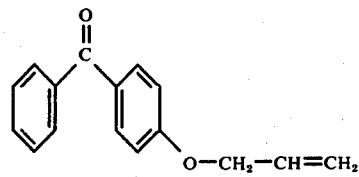 | m.p.: 74–75° C |

-continued
| Active Substance | Physical Data |
|---|---|
| 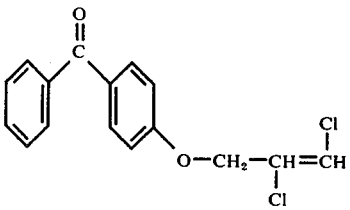 | m.p.: 53–57° C |
| 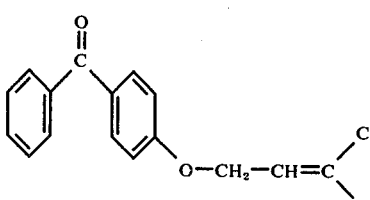 | m.p.: 80–81° C |
| 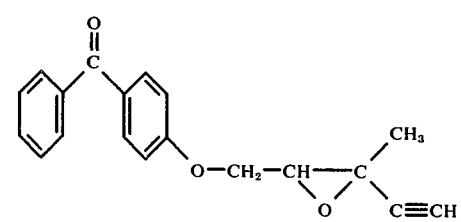 | $n_D^{20}$: 1,5954 |
| 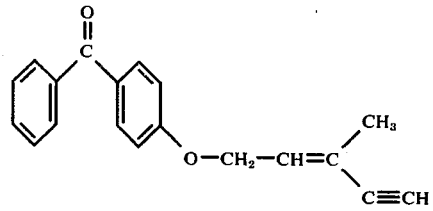 | $n_D^{20}$: 1,614 |
| 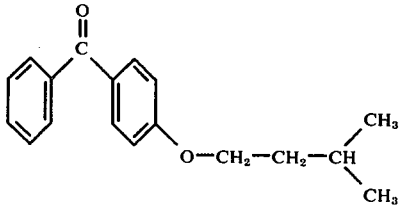 | $n_D^{20}$: 1,5762 |
| 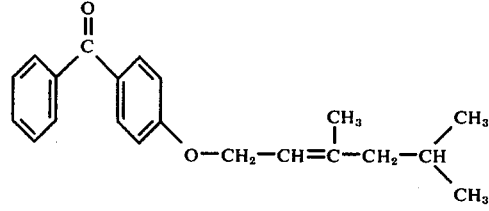 | $n_D^{20}$: 1,5738 |
| 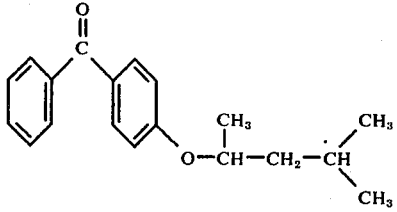 | $n_D^{20}$: 1,5571 |

-continued

| Active Substance | Physical Data |
|---|---|
| benzophenone-4-O-CH₂-CH₂-C(CH₃)(CH₂-CH₃)-OCH₃ | $n_D^{20}$: 1.5678 |
| benzophenone-4-O-CH₂-CH₂-C(CH₃)₂-O-CH₂-CH₃ | |
| benzophenone-4-O-CH₂-CH=cyclopentyl(H) | |
| benzophenone-4-CH₂-O-CH₂-CH=C(CH₃)₂ | |
| benzophenone-4-CH₂-O-CH₂-CH₂-C(CH₃)₂-OCH₃ | |
| 4-CH₃O-benzophenone-4'-O-CH₂-CH=C(CH₃)-CH₂-CH₃ | |

EXAMPLE 5

Stabilitory action on Dysdercus fasciatus larvae

10 Dysdercus fasciatus larvae are treated topically with solutions of active substance in acetone 8–10 days before they are due to shed and emerge to the adult stage. The larvae are then maintained at 28° C and 80–90% relative atmospheric humidity. They are fed with meal made from premoistened cotton seeds. After about 10 days, i.e. as soon as the untreated larvae have shed and emerged fully to the adult stage, the test subjects are examined.

Next to normal adults and desd larvae there are found special forms such as "super larvae" (larvae in which additional shedding occurs) and "adultoids" (adults with larval features).

The special forms are nonviable development stages which are not found in the normal development cycle.

The compounds according to Examples 1 to 4 displayed good activity in the above test.

EXAMPLE 6

Inhibitory action in the gas phase on eggs of Spodoptera littoralis 40 mg of active substance (direct) were put into a ground glass flask of 130 ml capacity and 100 eggs of Spodoptera littoralis were put into an other 175 ml of capacity. Both flasks were connected with a connecting piece and left to stand at 25° C.

The evaluation of the inhibitory action took place after 5 to 6 days. The compounds according to Examples 1 to 4 displayed good action in the above test.

I claim:

1. A compound of the formula

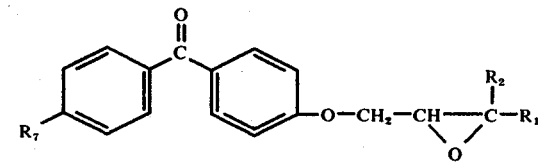

wherein $R_1$ represents alkyl with 1 to 4 carbon atoms, $R_2$ represents hydrogen, methyl or ethyl and $R_7$ represents hydrogen or methyl.

2. The compound according to claim 1 wherein $R_1$ represents methyl or ethyl.

3. 4-(2,3-epoxy-3-methyl-pentyl-1-oxy)-benzophenone, according to claim 2.

4. 4-(3-methyl-2,3-epoxy-butyl-1-oxy)benzophenone according to claim 2.

* * * * *